United States Patent [19]

Stefanchik et al.

[11] Patent Number: 5,601,574
[45] Date of Patent: Feb. 11, 1997

[54] STERILE CLIPS AND INSTRUMENT FOR THEIR PLACEMENT

[75] Inventors: David Stefanchik, Mason; Edward J. Biehle, IV, Westchester, both of Ohio

[73] Assignee: Ethicon, Inc., Cincinnati, Ohio

[21] Appl. No.: 425,964

[22] Filed: Apr. 20, 1995

Related U.S. Application Data

[60] Continuation of Ser. No. 144,926, Oct. 28, 1993, Pat. No. 5,474,567, which is a division of Ser. No. 944,584, Sep. 14, 1992, Pat. No. 5,342,373.

[51] Int. Cl.⁶ ........................................... A61B 17/04
[52] U.S. Cl. ..................................... 606/143; 606/139
[58] Field of Search ........................... 606/139, 142, 606/143, 151, 157, 158; 227/19, 901, 902

[56] References Cited

U.S. PATENT DOCUMENTS

| | | |
|---|---|---|
| 3,023,039 | 2/1962 | Henningsen et al. . |
| 3,098,232 | 7/1963 | Brown . |
| 3,363,628 | 1/1968 | Wood . |
| 3,518,993 | 7/1970 | Blake . |
| 3,631,707 | 1/1972 | Miller ............................... 606/142 |
| 3,757,629 | 9/1973 | Schneider . |
| 3,777,538 | 12/1973 | Weatherly et al. ............... 606/142 |
| 3,827,277 | 8/1974 | Weston . |
| 3,882,854 | 5/1975 | Hulka et al. ....................... 606/142 |
| 3,955,581 | 5/1976 | Spasiano .............................. 227/19 |
| 3,989,049 | 11/1976 | Yoon . |
| 4,027,510 | 6/1977 | Hiltebrandt ........................ 606/205 |
| 4,038,987 | 8/1977 | Komiya ............................ 606/142 |
| 4,064,881 | 12/1977 | Meredith . |
| 4,152,920 | 5/1979 | Green ............................... 606/143 |
| 4,169,476 | 10/1979 | Hiltebrandt . |
| 4,170,990 | 10/1979 | Baumgart et al. . |
| 4,196,836 | 4/1980 | Becht . |
| 4,217,902 | 8/1980 | March . |
| 4,226,239 | 10/1980 | Polk et al. . |
| 4,228,895 | 10/1980 | Larkin . |
| 4,246,903 | 1/1981 | Larkin . |
| 4,317,451 | 3/1982 | Cerwin . |
| 4,367,746 | 1/1983 | Derechinsky . |
| 4,374,523 | 2/1983 | Yoon . |
| 4,396,139 | 8/1983 | Hall et al. . |
| 4,418,694 | 12/1983 | Beroff et al. . |
| 4,433,689 | 2/1984 | von Zeppelin . |
| 4,471,766 | 9/1984 | Terayama . |
| 4,476,865 | 10/1984 | Failla et al. . |
| 4,485,816 | 12/1984 | Krumme . |
| 4,492,232 | 1/1985 | Green ............................... 606/143 |
| 4,493,319 | 1/1985 | Polk et al. . |
| 4,509,518 | 4/1985 | McGarry et al. . |
| 4,512,345 | 4/1985 | Green . |
| 4,527,562 | 7/1985 | Mericle . |
| 4,550,715 | 11/1985 | Santangelo et al. . |
| 4,557,263 | 12/1985 | Green . |
| 4,562,839 | 1/1986 | Blake, III et al. . |
| 4,590,937 | 5/1986 | Deniega ........................... 606/157 |
| 4,616,650 | 10/1986 | Green et al. ...................... 606/143 |
| 4,616,651 | 10/1986 | Golden ............................ 606/142 |
| 4,620,541 | 11/1986 | Gertzman et al. ............... 606/158 |
| 4,624,254 | 11/1986 | McGarry et al. ................ 606/143 |
| 4,637,395 | 1/1987 | Caspar et al. ................... 606/143 |
| 4,638,804 | 1/1987 | Jewusiak ......................... 606/142 |
| 4,646,741 | 3/1987 | Smith . |
| 4,658,822 | 4/1987 | Kees, Jr. .......................... 606/158 |

(List continued on next page.)

FOREIGN PATENT DOCUMENTS

| | | |
|---|---|---|
| WO88/01486 | 3/1988 | European Pat. Off. . |
| WO88/01487 | 3/1988 | European Pat. Off. . |
| 2330182 | 1/1975 | Germany ........................ 606/142 |
| 2730691 | 1/1978 | Germany . |
| 3802651 | 8/1989 | Germany ........................ 606/142 |
| 4015562 | 11/1991 | Germany . |
| 90/03763 | 4/1990 | WIPO . |
| WO95/05778 | 3/1995 | WIPO . |

*Primary Examiner*—Gary Jackson
*Attorney, Agent, or Firm*—Dressler, Goldsmith, Milnamow & Katz, Ltd.

[57] ABSTRACT

An improved surgical instrument and sterile clip for ligating the vessel of a mammal. The clip has a pair of legs which are urged apart by the instrument to allow the clip to be placed on the vessel to be ligated.

26 Claims, 12 Drawing Sheets

U.S. PATENT DOCUMENTS

| | | |
|---|---|---|
| 4,662,373 | 5/1987 | Montgomery et al. . |
| 4,665,906 | 5/1987 | Jervis . |
| 4,671,278 | 6/1987 | Chin . |
| 4,696,396 | 9/1987 | Samuels . |
| 4,702,247 | 10/1987 | Blake et al. . |
| 4,712,549 | 12/1987 | Peters et al. . |
| 4,741,337 | 5/1988 | Smith et al. . |
| 4,765,335 | 8/1988 | Schmidt et al. . |
| 4,777,949 | 10/1988 | Perlin . |
| 4,777,950 | 10/1988 | Kees, Jr. . |
| 4,788,966 | 12/1988 | Yoon . |
| 4,791,707 | 12/1988 | Tucker . |
| 4,796,625 | 1/1989 | Kees, Jr. . |
| 4,796,627 | 1/1989 | Tucker . |
| 4,821,721 | 4/1989 | Chin et al. . |
| 4,822,348 | 4/1989 | Casey . |
| 4,834,096 | 5/1989 | Oh et al. . |
| 4,844,066 | 7/1989 | Stein . |
| 4,858,608 | 8/1989 | McQuilkin . |
| 4,869,268 | 9/1989 | Yoon . |
| 4,919,152 | 4/1990 | Ger . |
| 4,944,443 | 7/1990 | Oddsen et al. . |
| 4,950,258 | 8/1990 | Kawai et al. . |
| 4,976,722 | 12/1990 | Failla . |
| 4,983,176 | 1/1991 | Cushman et al. . |
| 5,002,563 | 3/1991 | Pyka et al. . |
| 5,026,379 | 6/1991 | Yoon . |
| 5,035,692 | 7/1991 | Lyon et al. ............................ 606/143 |
| 5,037,433 | 8/1991 | Wilk et al. . |
| 5,044,540 | 9/1991 | Dulebohn . |
| 5,053,045 | 10/1991 | Schmidt et al. . |
| 5,084,057 | 1/1992 | Green et al. . |
| 5,100,420 | 3/1992 | Green et al. . |
| 5,156,609 | 10/1992 | Nakao et al. ........................... 606/142 |
| 5,207,692 | 5/1993 | Kraus ..................................... 606/143 |
| 5,217,473 | 6/1993 | Yoon ...................................... 606/157 |
| 5,389,098 | 2/1995 | Tsuruta et al. ........................... 606/41 |
| 5,395,381 | 3/1995 | Green et al. ............................ 606/143 |

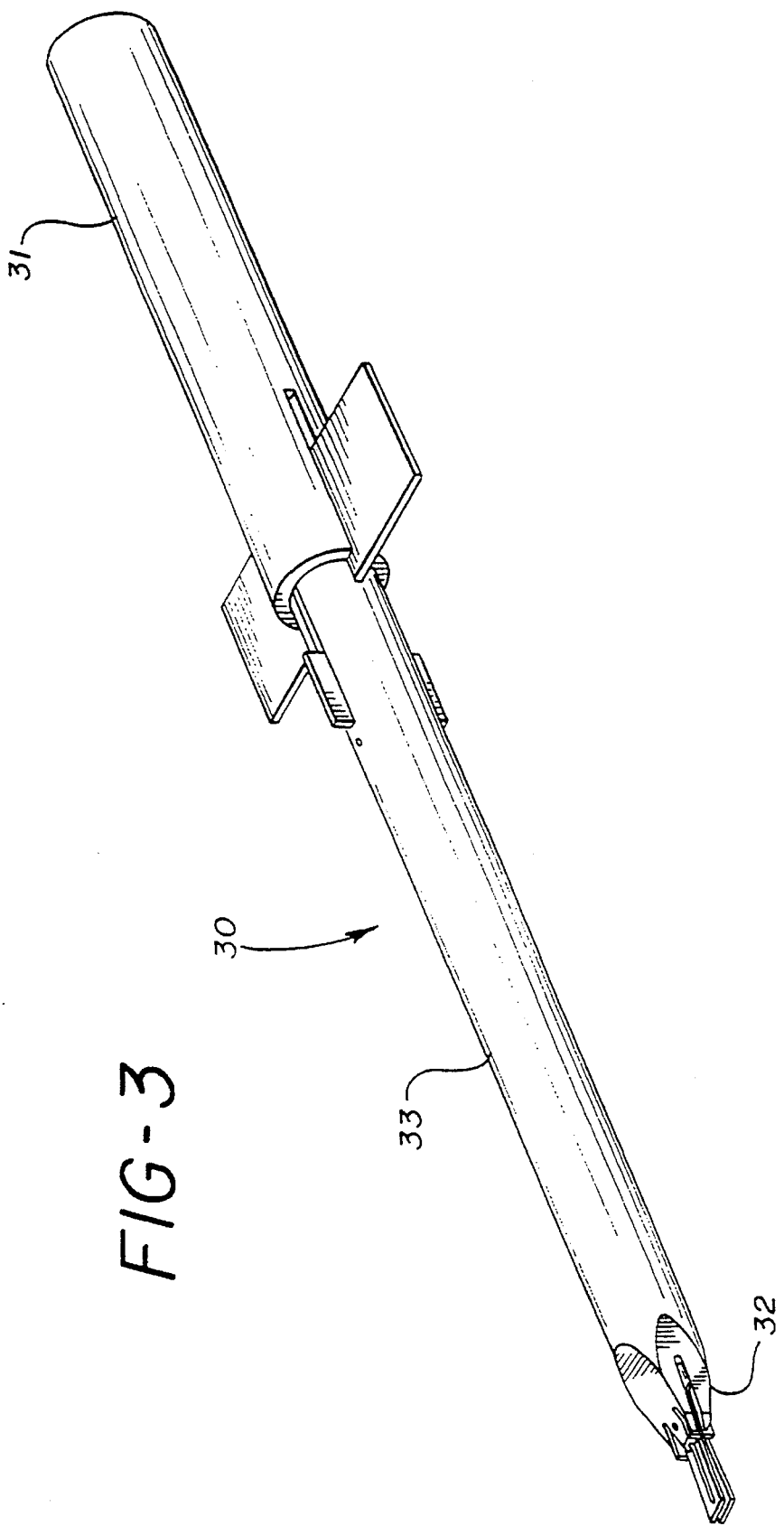

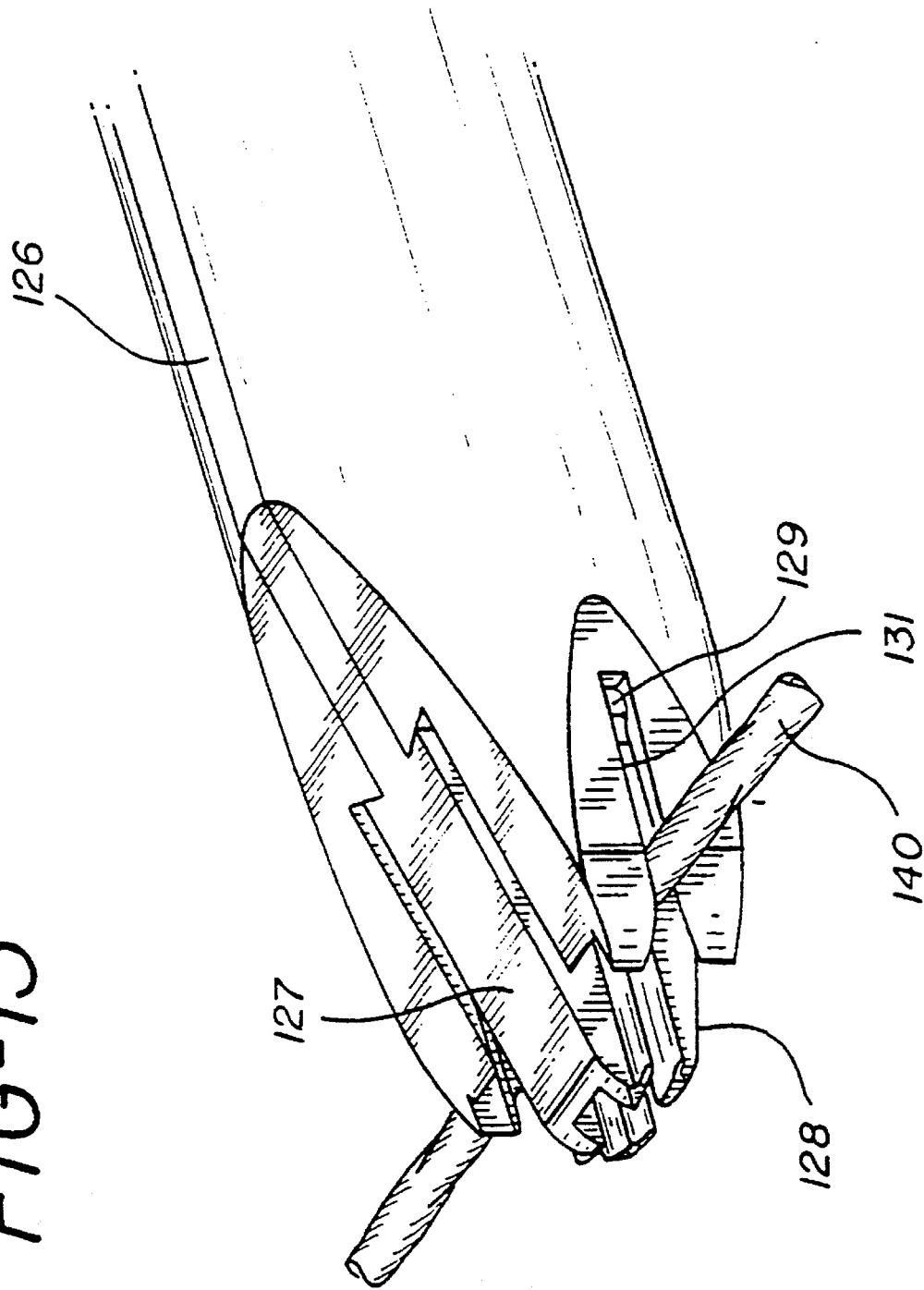

STERILE CLIPS AND INSTRUMENT FOR THEIR PLACEMENT

This is a continuation, of application Ser. No. 08/144,926filed Oct. 28, 1993, which is a division of Ser. No. 07/944,584, filed Sep. 14, 1992, now U.S. Pat. No. 5,342,373, which is hereby incorporated by reference.

BACKGROUND OF THE INVENTION

The present invention relates to sterile clips used to ligate vessels in mammals and more particularly to sterile clips that are used to close or shut tubular vessels such as blood vessels within the body and to instruments for placing such clips on a vessel to ligate the vessel.

During many surgical procedures the surgeon will have to ligate or close various blood vessels before severing those vessels in order to prevent excessive bleeding during the surgical procedure. There are many types of mechanisms or devices for shutting off the vessel such as ligating clips, hemostatic clips and the like. In some instances the surgeon will tie a ligature or suture about the vessel to close or shut the vessel. Many of the clips are metal and comprise a pair of legs which are connected at one end. The vessel to be ligated is placed between the legs and the legs forced together about the vessel to close the vessel. Clips have also been developed from plastic materials but because plastics don't have the same stress and resiliency characteristics as metals, usually the plastic clips include some type of locking mechanism so that when the legs are urged together about the vessel they are locked in a closed position. Ligating clips are well know in the art and are disclosed in numerous U.S. Pat. Nos. as for example, 3,439,523; 3,270,745; 3,363,628; 3,463,156; 3,439,522; 4,146,130; 4,449,530; 4,424,810; 4,418,694; and 4,638,804.

Ligating clips must ensure closure of the vessel. That is, they should completely shut off blood flow and not allow leakage. Also, the clips must remain closed and should not "pop" open or break because of undue stresses. Such opening or breaking would have disastrous results during surgery. Furthermore, the clips should not slip or slide out of position or off the vessel completely. While it doesn't take much force to collapse and close a vessel, the clips, to ensure closure of that vessel and to ensure that they remain in their closed position, require substantial force to close or change the configuration of the clip so that once closed it will remain in its closed position.

With the advent of endoscopic surgery, it has become very important to substantially reduce the forces to carry out virtually any of the manipulations required in an endoscopic surgical procedure such as ligating a vessel. In endoscopic surgery, while the business end of the instrument is placed within the body through an appropriate cannula or small incision, the manipulation of that business end by the surgeon is accomplished outside the body. As a result, it becomes more difficult to control the business end of the instrument since it is further removed from the actual operation of the instrument and any slight movement in the manipulation of the instrument outside the body is magnified at the business end of the instrument. Therefore, the greater the force required to close a clip the greater the possibility of movement of the business end of the instrument and the greater the possibility that the clip is improperly placed or improperly closed.

The present invention substantially reduces the forces required to ligate a vessel. The present invention also provides a clip that ensures closure of the vessel once the clip is placed on the vessel. Furthermore, the present invention allows for ligating clips to be made from many different types of materials such as metals, plastics and the like.

Though the novel clip and instrument of the present invention is most appropriate for use in endoscopic procedures and will be so described in the following description it should be pointed out that the clip and/or the instrument could also be used in laparoscopic procedures and even standard open type surgical procedures.

SUMMARY OF THE PRESENT INVENTION

In accordance with the present invention, our new sterile clip for ligating a vessel in a mammal comprises a pair of leg members. The leg members are disposed in close proximity to one another along substantially their entire length. Preferably, the leg members are substantially parallel to each other. The leg members are connected, preferably at one end thereof, by a member which restricts separation of the leg members. The connecting member should allow the open end of the leg members to be slightly pushed apart by forces applied to the open end of the leg member, but once those forces are removed the leg members should return to their original position.

The present invention also includes an instrument for applying the sterile clip as described above to a vessel to be ligated. Our new instrument includes a pair of surfaces with the surfaces diverging from each other from their proximal end to their distal end. These surfaces will accept a vessel to be ligated. That is, the surfaces may be placed on opposite sides of the vessel to be ligated. Once the vessel is appropriately positioned, the sterile clip as described above has its open end urged over the proximal end of the diverging surfaces. The diverging surfaces spread the legs of the clip slightly and the clip is slipped over the diverging surfaces. The diverging surfaces are closed or brought to a substantially parallel position to ligate the vessel positioned between the surfaces. Once the clip has been placed over the surfaces with the vessel therebetween, the clips are removed from the diverging surfaces and the clip remains on the ligated vessel. The diverging surfaces may then be removed from about the vessel.

The invention will be more fully described in conjunction with the specific embodiments given in the following drawings and description.

DESCRIPTION OF THE DRAWINGS

FIG. 3 is a perspective view of one embodiment of an instrument of the present invention;

FIG. 15 is a view similar to FIG. 13 after the instrument has been actuated.

DETAILED DESCRIPTION OF THE INVENTION

Figure 2:
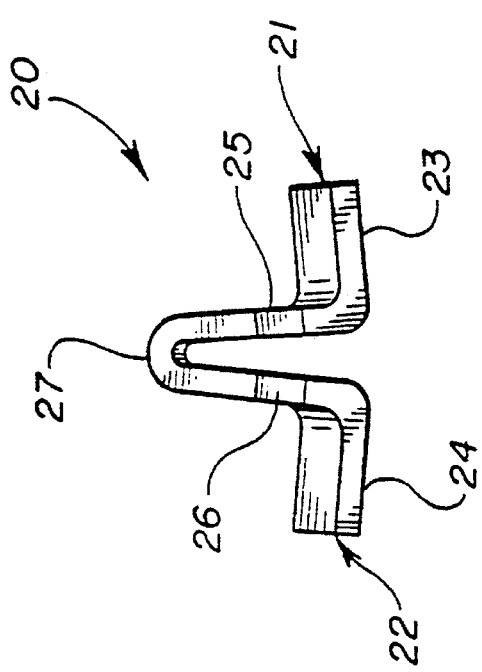
FIG. 2 is a front view of a sterile clip of the present invention.
Figure 1:
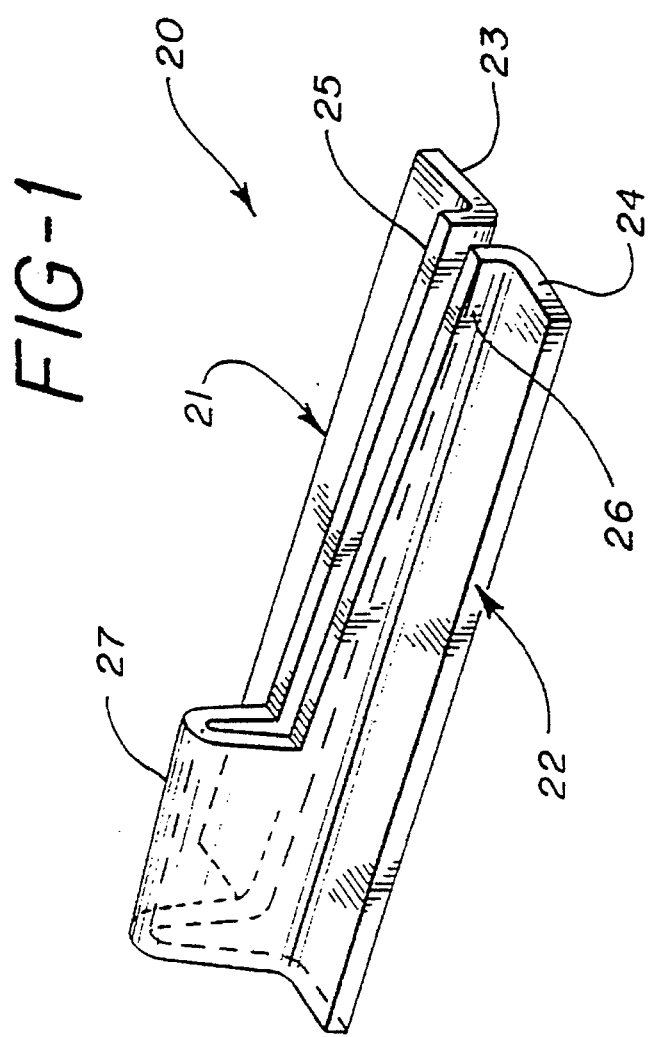
FIG. 1 is a perspective view of a sterile clip of the present invention.

Referring to the drawings in FIGS. 1 and 2, there is shown a preferred embodiment of the sterile clip of the present invention. The clip is used to ligate or close tubular vessels in a mammal and more specifically, to close blood vessels in the body of a human during endoscopic surgical procedures. The sterile clip 20 comprises a pair of leg members 21 and 22. The leg members are in close proximity to one another along their entire length. In the embodiment, each of the leg members is a right angle member and comprises a relatively flat Longitudinal section 23 and 24 and a perpendicular section 25 and 26 extending from one edge of a longitudinal section. The perpendicular sections of the leg members face each other and are the portion of the clip which contact the vessel to ligate the vessel. The perpendicular sections are joined together at one end of the clip by a connecting member 27 which has a cross-sectional shape similar to that of a "horse-shoe" as shown. The connecting member restricts separation of the Leg members from each other. In certain embodiments of the sterile clip of the present invention, the connecting member is made of resilient material so that the legs may be slightly parted to insert the already closed vessel and once inserted the leg members are allowed to return to their original position to maintain the vessel ligated.

Ligating clips may be applied to blood vessels during a surgical procedure either as a single clip using a single clip applier or utilizing a multiple clip applier. The instrument may be inserted through a cannula during an endoscopic procedure and if a multiple clip applier is being used the instrument may ligate or place clips on a number of vessels. Often in a surgical procedure there is a technique called ligate and divide. In this technique, an instrument is used to place two ligating clips on the same vessel in relatively close proximity and the surgeon either utilizing an appropriate instrument or a scalpel will cut the vessel between the two ligating clips. In FIG. 3 there is shown a ligating and dividing instrument utilizing the sterile clips and instrument of the present invention. The instrument 30 comprises a handle portion 31 which contains various actuating and control mechanisms for the surgeon and a nose portion 32 which places the clips and cuts the vessel between appropriately placed clips. The nose portion is connected to the handle portion by a magazine housing 33 which is designed to fit through a cannula to allow the nose portion to be positioned within the surgical environment and accomplish the desired tasks.

Figure 4:
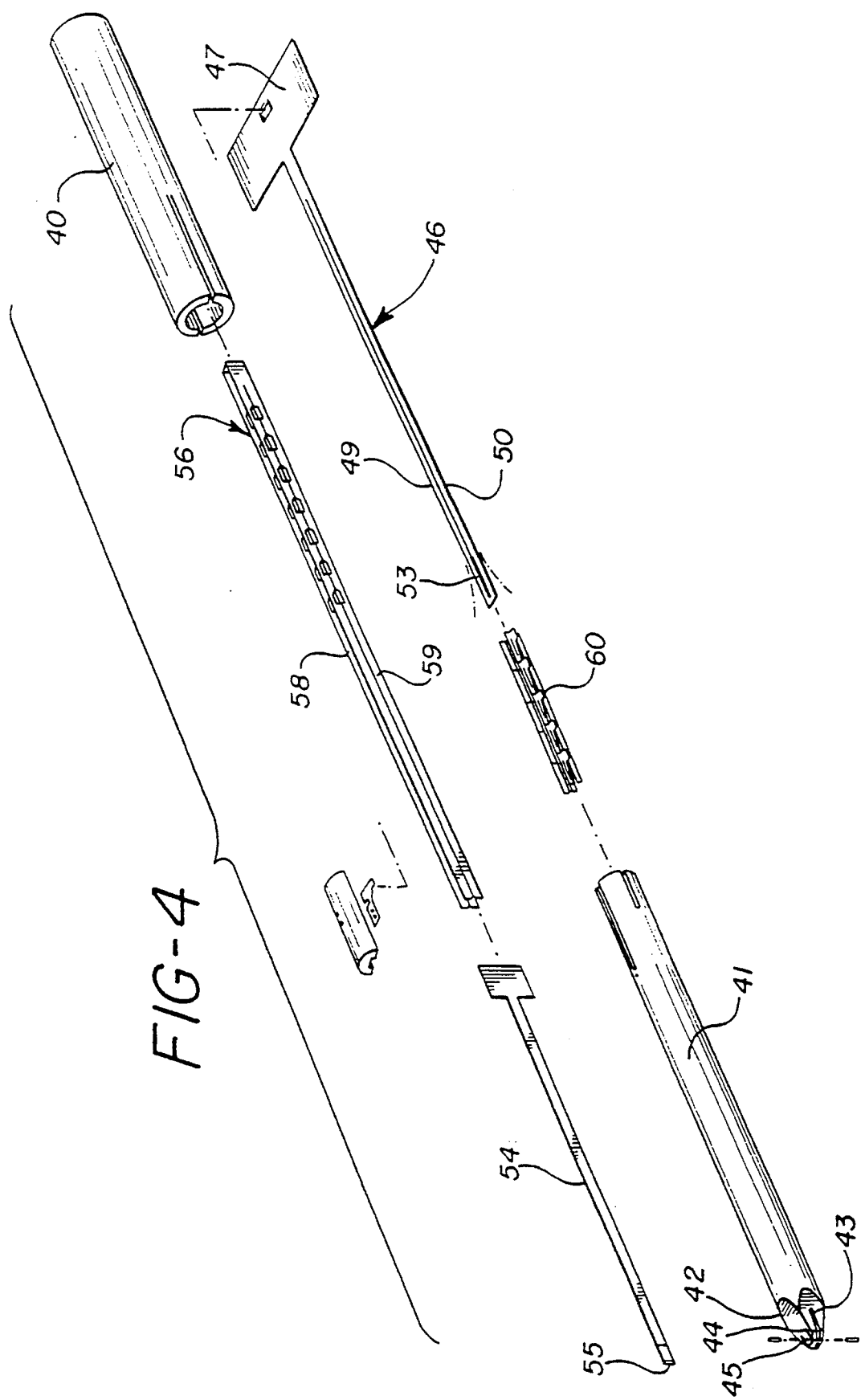
FIG. 4 is an exploded isometric view of the instrument depicted in FIG. 3.

FIG. 4 is an expanded isometric view of the various parts of the instrument depicted in FIG. 3. The instrument comprises a handle 40 and attached to one end of the handle is a magazine housing 41. One end of the housing is attached to the handle while the opposite end of the housing is the nose 42 or business end of the instrument and is designed to place clips in accordance with the present invention. The nose or business end of the magazine housing contains a horizontal slot 42 disposed substantially in the center of the nose and two perpendicular slots 44 and 45 disposed perpendicular and adjacent to opposite ends of the horizontal slot. Positioned within the magazine housing and extending from the handle to the nose is a tweezer member 46. A portion of this member grips the vessel to be ligated. One end 47 of the tweezer member is positioned within the handle so that the handle and/or magazine housing may be reciprocated back and forth with respect to the tweezer member. The opposite end of the tweezer member fits into the horizontal slot in the nose of the magazine. This end of the tweezer member comprises a pair of spring steel flaps 49 and 50 joined together at the end proximal to the handle and stressed in such a manner that they deflect from each other at the end distal to the handle. In the forward most position of the magazine the spring steel end of the tweezer member is aligned with the end of the nose of the magazine housing. In the rearwardmost position of the magazine housing the spring steel end of the tweezer member extends through the horizontal slot and beyond the nose of the magazine housing. Extending substantially the length of the tweezer member is a slot 53. A knife member 54 is positioned to reciprocate back and forth in this slot. The cutting portion 55 of the knife member in its forward-most position extends to the tip of the tweezer member and in its rearwardmost position is spaced a short distance therefrom. Also contained within the magazine housing is a clip driver 56. The driver comprises a pair of metal legs 58 and 59 which extend from the handle to the nose of the magazine housing. One leg of the driver fits within one perpendicular slot in the nose of the housing and the other leg of the driver fits into the other perpendicular slot in the nose of the housing. Positioned on the front end of the driver is a clip cartridge 60. In this embodiment there are ten clips shown, five on each side aligned with a leg of the driver. The appropriate actuating members for moving the magazine housing, positioning the clips, driving the clips and moving the knife or reciprocating the knife are provided in the handle.

Figure 5A:
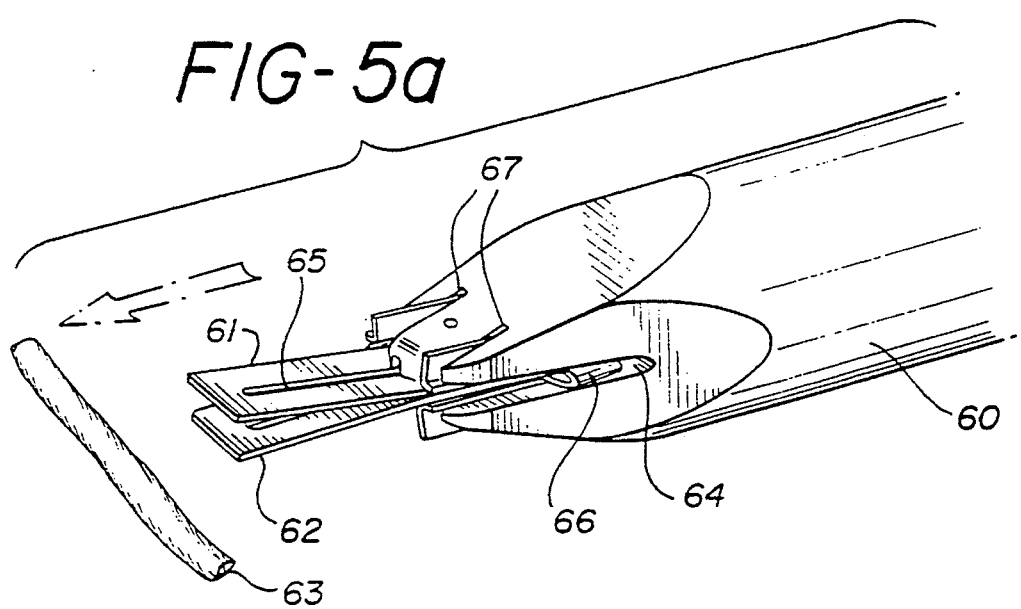
FIGS. 5 a, b and c are a perspective view, top view and side view, respectively, of the nose or business end of an instrument according to the present invention with the instrument in a position to accept a vessel to be ligated.
Figure 5B:
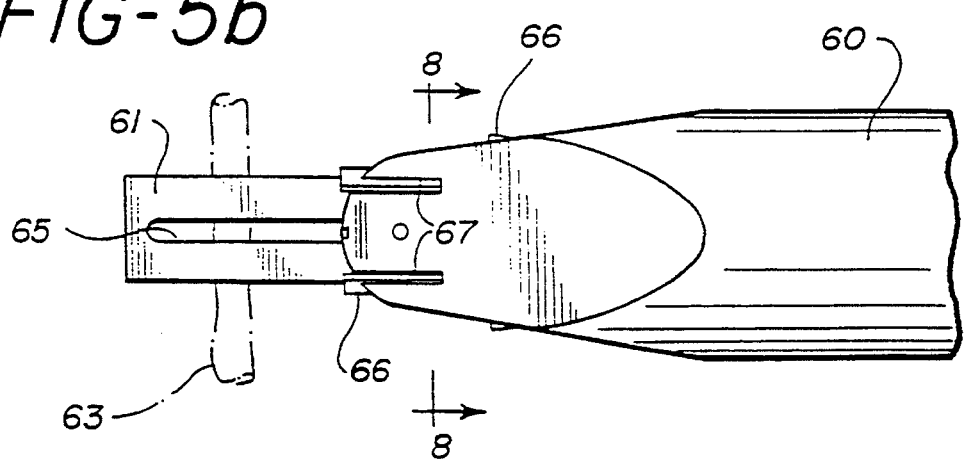
Figure 5C:
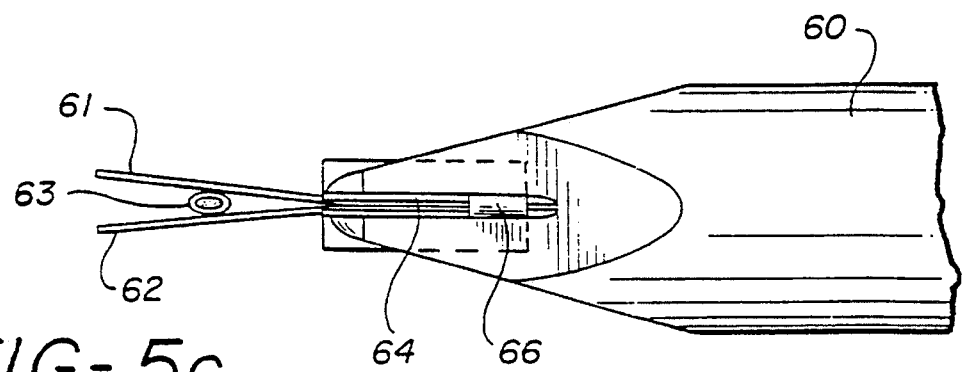
Figure 6A:
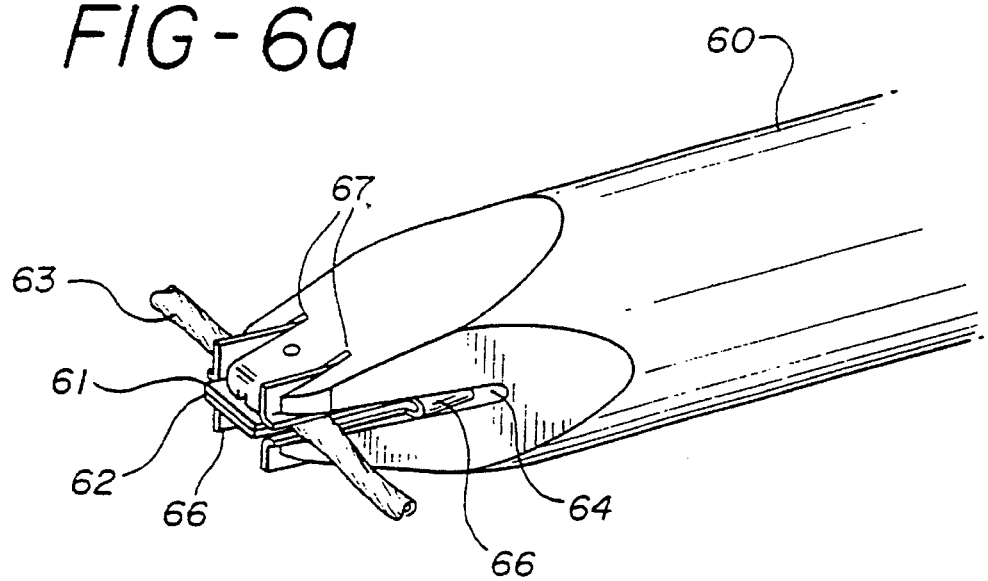
FIGS. 6 a, b and c are a perspective view, top view and side view, respectively, of the nose of the instrument depicted in FIG. 5 wherein a sterile clip of the present invention has been placed on the vessel to ligate the vessel.
Figure 6B:
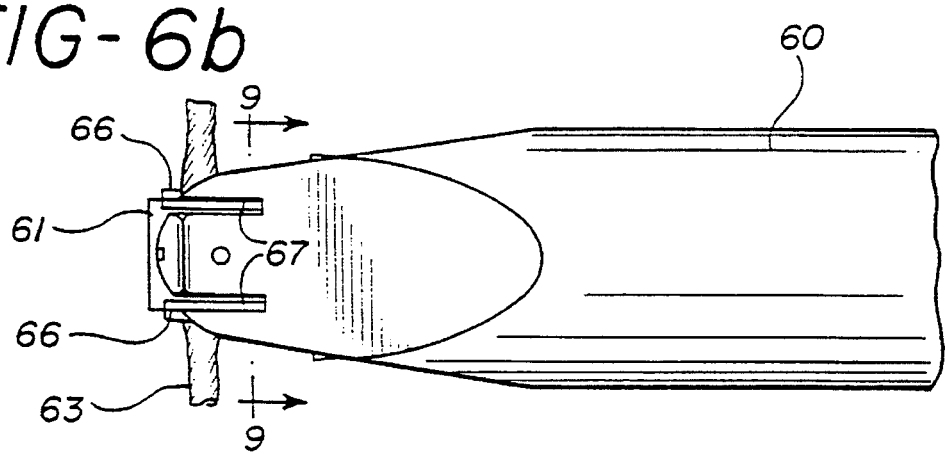
Figure 6C:
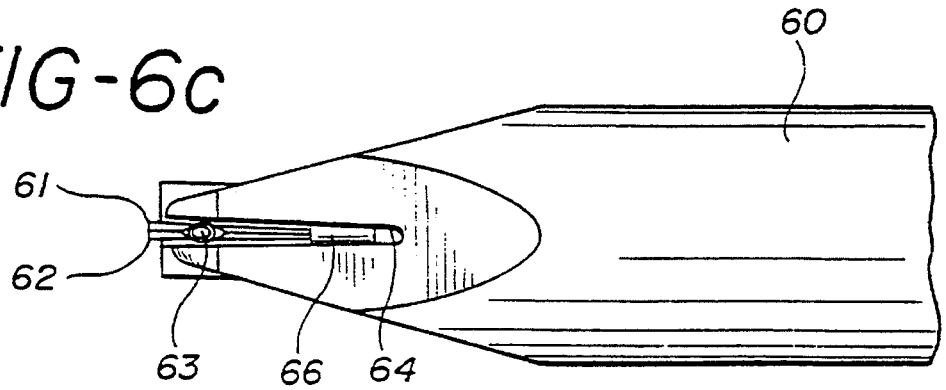
Figure 7A:
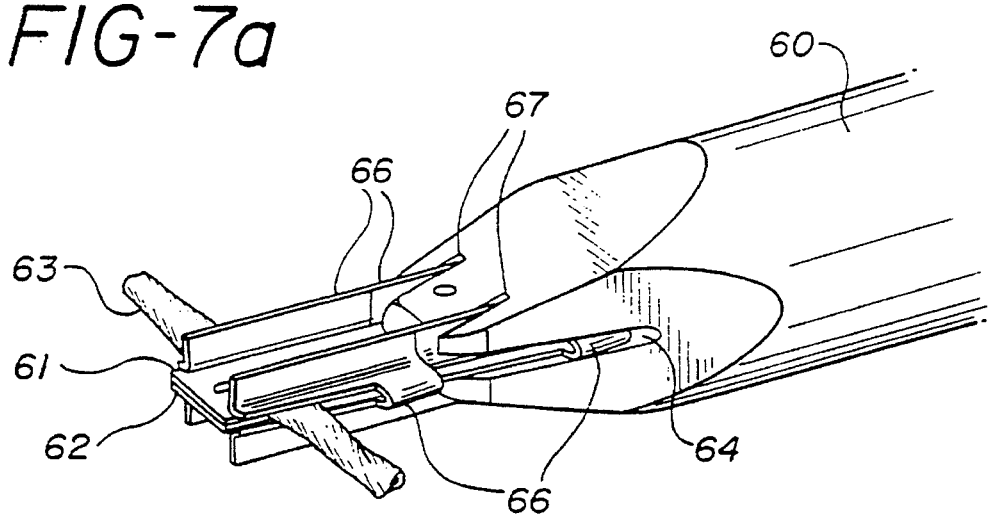
FIGS. 7 *a, b* and *c* are a perspective view, top view and side view, respectively, of the nose of the instrument depicted in FIG. 5 with the instrument positioned to release the ligated vessel from the instrument.
Figure 7B:
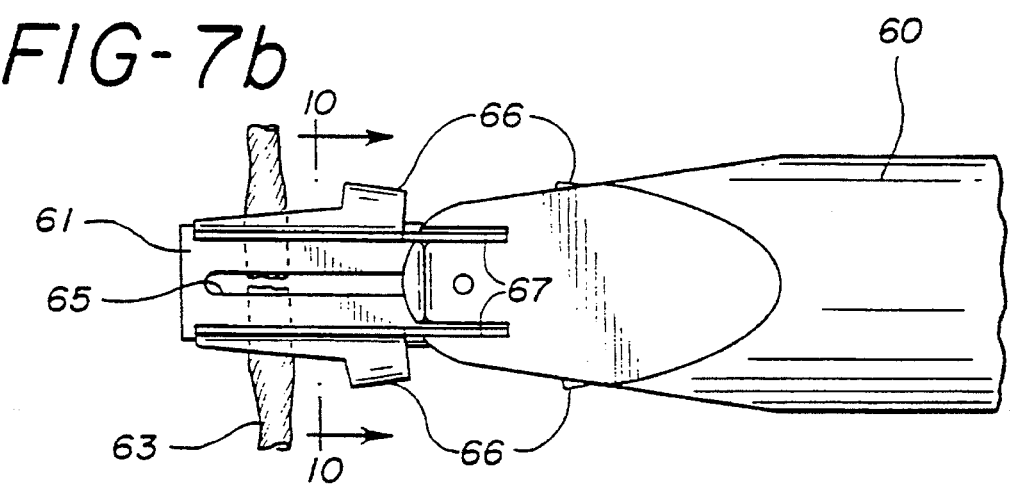
Figure 7C:
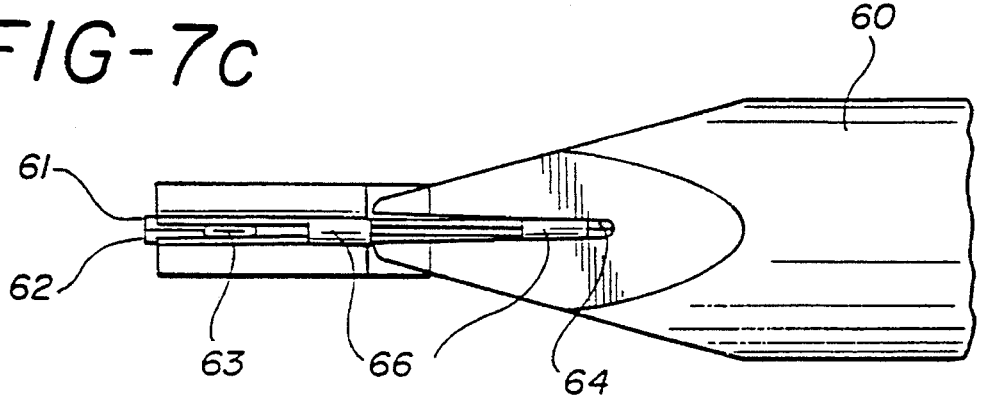

The operation of the instrument will be more fully described in conjunction with FIGS. 5, 6 and 7. Referring to FIGS. 5*a, b* and *c*, there is shown an enlarged view of the nose portion of an instrument as described in conjunction with FIG. 4. FIG. 5*a* is a perspective view of the nose section, FIG. 5*b* is a top view and FIG. 5*c* is a side view. In these Figures, the nose portion 60 has been pushed to its rearwardmost position. The two surfaces 61 and 62 of the tweezer portion extend beyond the nose and diverge from each other to accept a vessel 63 to be ligated. As more clearly shown in FIG. 5*c*, the tweezer portion extends through the horizontal slot 64 in the nose portion. There also is depicted the slot 65 in the tweezer portion which allows for movement of the knife. As may be seen in this position of the instrument, the clips 66 are in place and positioned in the perpendicular slots 67 in the nose portion. Once the diverging surfaces of the tweezer portion are placed about the vessel, the nose portion may be pushed forwardly. The nose portion pushed to its forwardmost position is shown in FIGS. 6 *a, b* and *c*. FIG. 6*a* is a perspective view of the nose portion in its forwardmost position, FIG. 6b is a top view and FIG. 6*c* is a side view. By moving the magazine portion 60 forwardly, the tweezers surfaces 61 and 62 are brought together to close the vessel 63. Simultaneously, the clips 66 are moved forwardly so that the open end of a clip rides over the tweezer surfaces. At this point, the knife may be actuated to sever the vessel between the clips. The next step is to bring the magazine housing 60 back to its rearwardmost or original position which is depicted in FIGS. 7*a, b* and *c*. As may be seen, the tweezer surfaces 61 and 62 extend forwardly from the nose portion and are held together by the clips 66 which ride on the very outer edges of the tweezer surfaces. Once the clips are totally free from the nose of the magazine, they will drop or be removed from the tweezer surfaces. This will allow the tweezer surfaces to open and release the ligated and divided vessel 63.

Figure 8:
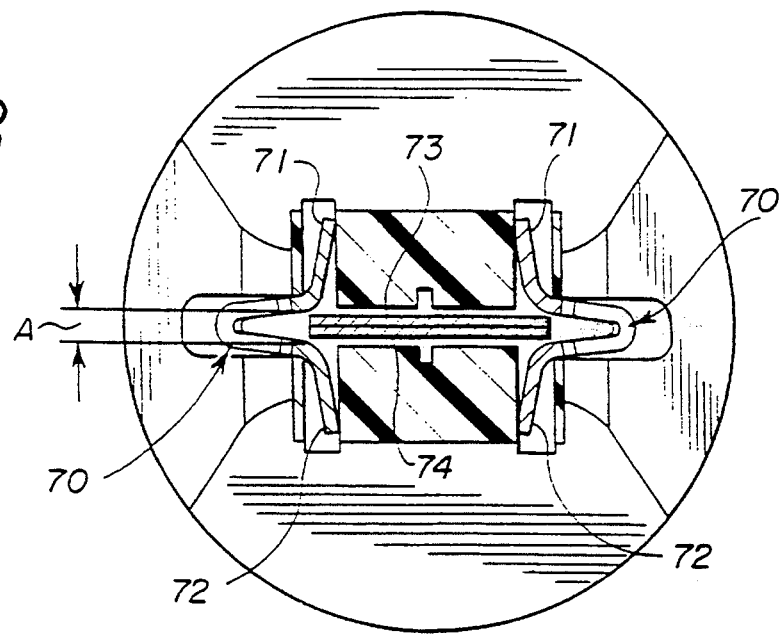
FIG. 8 is an enlarged cross-sectional view taken along line 8—8 of FIG. 5*b*.
Figure 9:
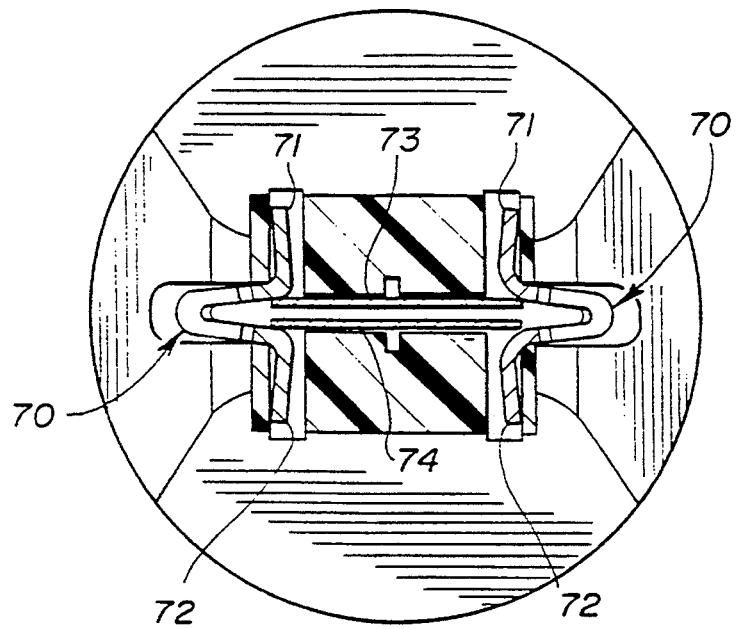
FIG. 9 is an enlarged cross-sectional View taken along line 9—9 of FIG. 6*b*.
Figure 10:
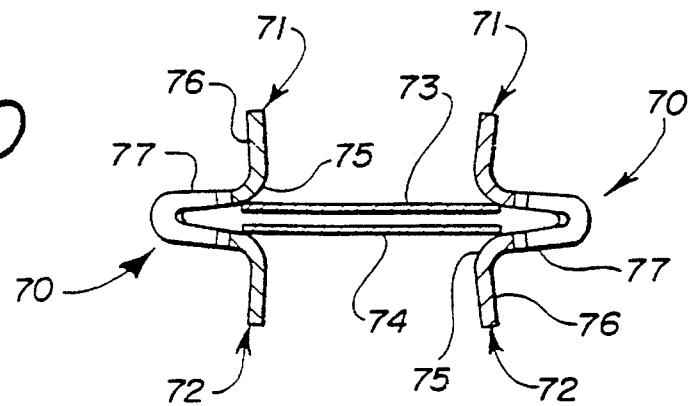
FIG. 10 is an enlarged cross-sectional view taken along line 10—10 of FIG. 7*b*.

The action of the clips in closing the vessel and the release of the clips from the tweezer surfaces may be more fully understood by referring to FIGS. 8, 9 and 10 which are enlarged cross-sectional views of the nose of the instrument as depicted in FIGS. 5*b*, 6*b*, and 7*b*, respectively. Referring to FIG. 8 the clips 70 are shown in the nose of the instrument in the position they have before being placed on a vessel. The legs 71 and 72 of the clip are in a position where there is the smallest gap (A) between the legs. FIG. 9 shows the nose portion of the instrument as shown in FIG. 6*b*. The nose portion is in its forwardmost position to push the clips 70 over the tweezer surfaces 73 and 74 and close a vessel. As may be seen, the tweezer surfaces tend to open the gap (A) between the legs of the clip slightly to allow the clip to move over the tweezer surfaces. Once this is accomplished, the clips remain on the tweezer surfaces as the magazine is brought to it rearward nose position.

This frees the tweezer surfaces from the nose and because the tweezer surfaces are stressed to diverge from each other, they place a force on the curve 75 between the perpendicular leg 76 and the horizontal leg 77 of the clip so that the clip is removed or slides off in a sideways manner from the tweezer surfaces.

Figure 11:
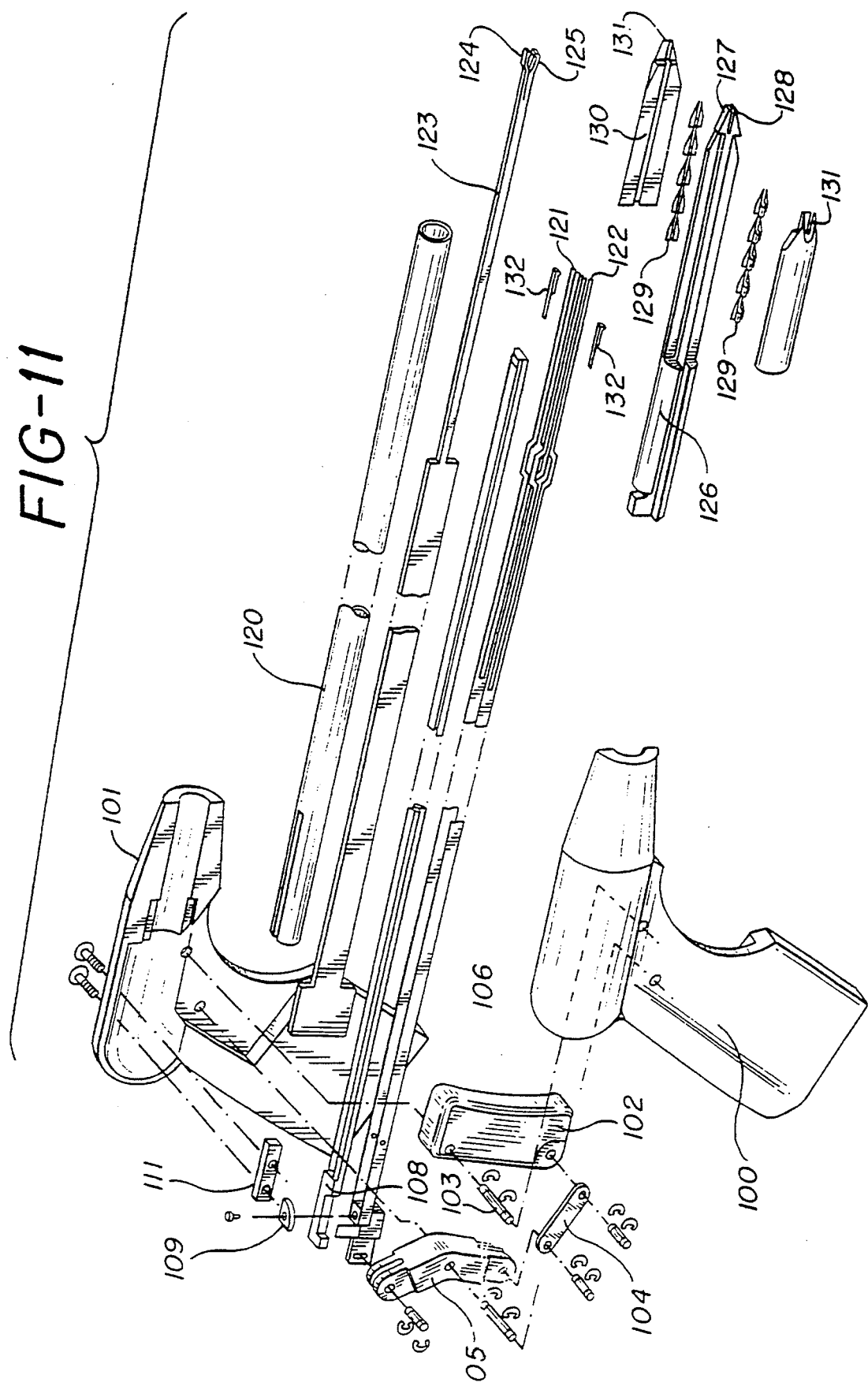
FIG. 11 is an exploded perpective view of another embodiment on an instrument of the present invention.

Referring to FIG. 11 of the drawings, there is shown an exploded view of another embodiment of a clip applier instrument according to the present invention. In this embodiment, the instrument comprises a right handle half 100 and a left handle half 101. Positioned between the handle halves is a trigger mechanism 102. The trigger mechanism is pivotally mounted on a pivot pin 103 between the handle halves. Attached at the bottom of the trigger mechanism is a drive link 104 which in turn is attached to the bottom of the drive pusher 105. Attached to the drive pusher is a first drive bar 106. As is more clearly seen in FIG. 12, a tab 107 extends upwardly from the first drive bar at the proximal end thereof. This tab fits in a slot at the rear or proximal end of a second drive bar 108. The second drive bar sits on top of the first drive bar. Mounted on top of the second drive bar is a pivotal timing tab 109. When the trigger mechanism is squeezed, the drive link forces the drive pusher forward. Both the first and second drive bars are also urged forwardly. The first drive bar is urged forwardly by the drive pusher and the second drive bar is urged forwardly by the upstanding tab 107 pushing the timing tab 109. When the timing tab moves to the end of the timing plate 111, it is pivoted out of the way of the upstanding tab. This stops the forward motion of the second drive bar while allowing the first drive bar to continue its forward motion as the trigger is squeezed. On release of the trigger, a standard leaf spring mechanism (not shown for the sake of clarity) returns the trigger mechanism, drive pusher and drive bar to their original positions.

Extending from the front of the handle halves is a hollow support tube 120. The first and second drive bars are disposed within the support tube. At the distal end of the first drive bar and attached thereto is a pair of spaced apart clip drivers 121 and 122. Also mounted on the handle halves and extending down the support tube is a tweezer mechanism 123. The tweezer mechanism terminates at the distal end of the instrument in opposed grasping fingers 124 and 125 disposed between the pair of clip drivers, as is more clearly shown in FIG. 13. Attached to the distal end of the second drive bar is the tweezer actuating means 126. The means terminates at its distal end in a pair of stationary spaced apart fingers 127 and 128 which when moved forwardly will encompass the tweezer fingers to close the fingers about a vessel placed between the tweezer fingers. A series of ligating clips 129 are stored in groves 130 disposed on opposite sides of the stationary fingers. The clip drivers terminate at their distal end in abutting relationship to the last clip in the series of clips. The clips are configured as shown in FIG. 1 with the U-shaped portion of the clip riding in the open grooves 131 at the distal end of the twezer actuating means. The U-shaped portion of the clip is engaged by a flexible dog 132 attached to the clip drivers. The flexibility of the dog allows it to ride over the next clip in the series when the clip drivers are retracted.

Figure 12:
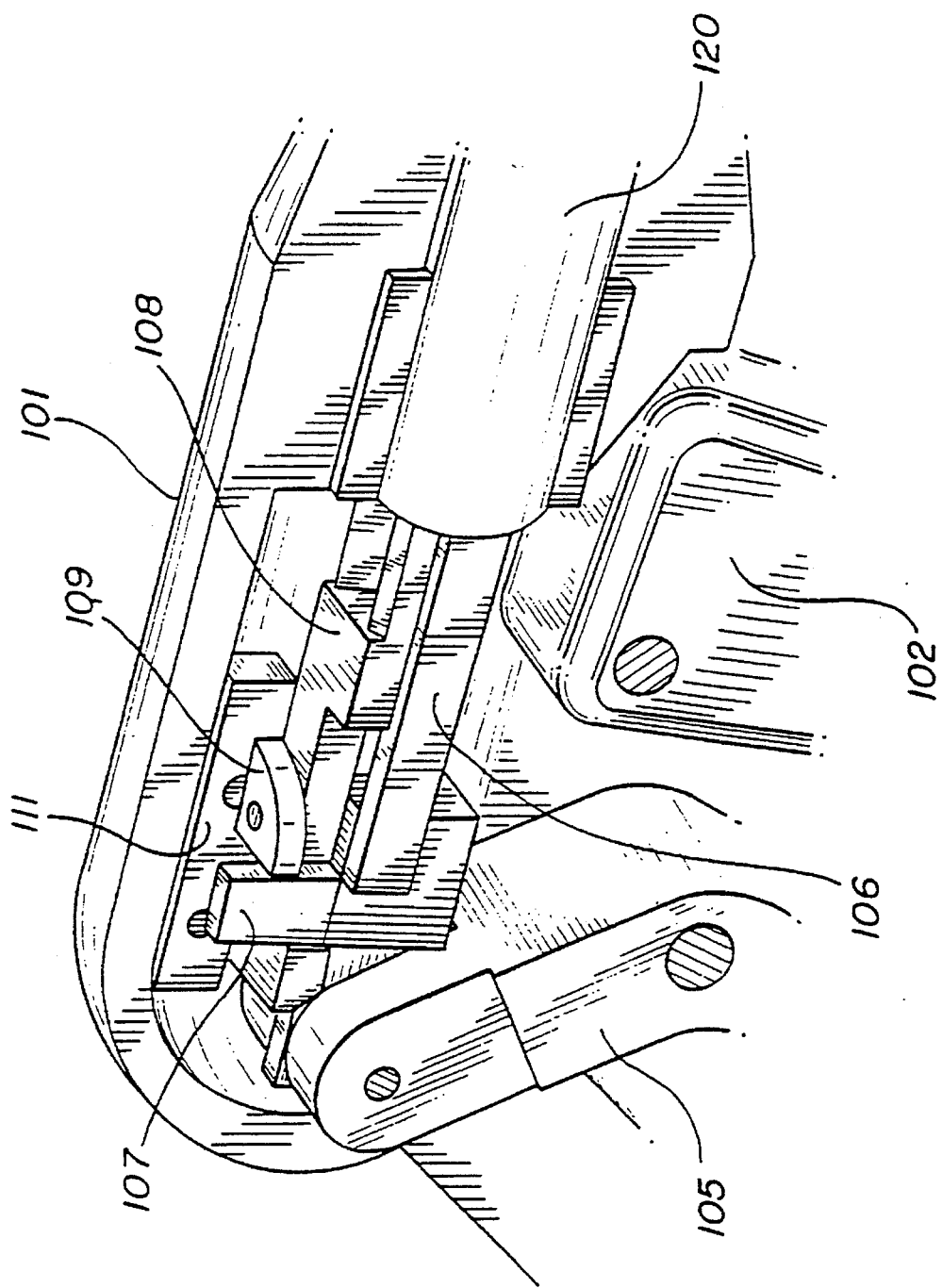
FIG. 12 is an enlarged cut-away perspective view of the drive mechanism of the instrument depicted in FIG. 11 before the instrument has been actuated.
Figure 13:
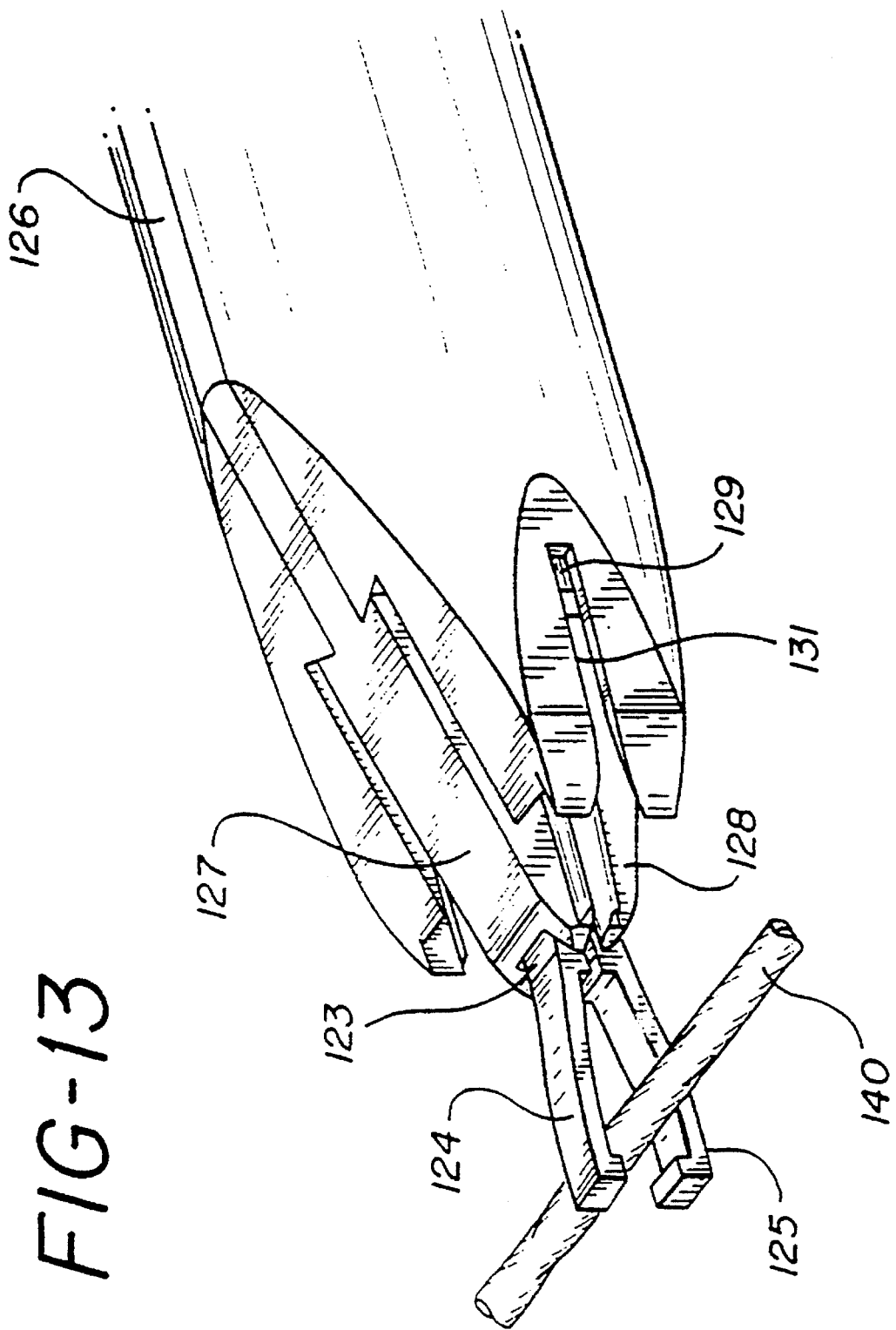
FIG. 13 is an enlarged perspective view of the distal end of the instrument depicted in FIG. 11 before the instrument has been actuated.
Figure 14:
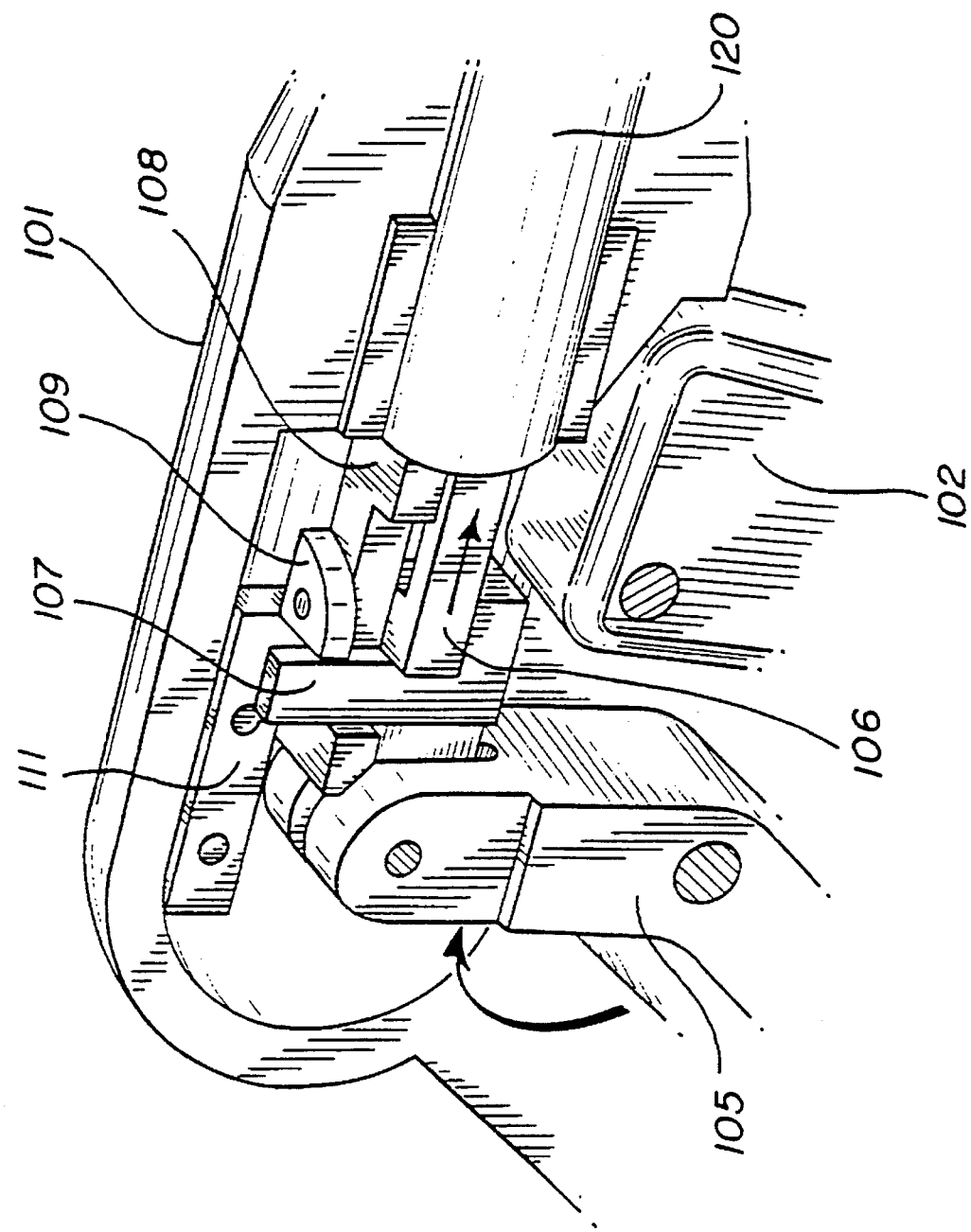
FIG. 14 is a view similar to FIG. 12 after the instrument has been actuated.

Referring to FIGS. 12 and 13, there is shown in FIG. 12 an enlarged cut-away view of the driving mechanism within the handle. FIG. 13 is a perspective view of the distal end of the instrument. Both Figures show the instrument prior to the trigger being operated. As shown in FIG. 12, the upstanding tab 107 on the first drive bar 106 is positioned behind the timing tab 109 on the second drive bar. In this position, the distal end of the instrument is as shown in FIG. 13 and a vessel 140 to be closed is positioned between the tweezer fingers 124 and 125. On squeezing the trigger, the first drive bar moves forwardly pushing the timing tab and the second drive bar forwardly to the position shown in FIG. 14. When the drive mechanism is in this position, the distal end of the instrument is as shown in FIG. 15. The second drive bar has pushed the stationary fingers 127 and 128 over the tweezer fingers 124 and 125 to close the vessel between the fingers. Simultaneously, the first drive bar has pushed the series of clips fowardly so that the first clip in each series is immediately adjacent the vessel shown in FIG. 15.

On continuing to squeeze the trigger, the first bar urges the clips over the vessel to close the vessel and moves the clips off the distal end of the clip driver tracks 121 and 122. On releasing the trigger, both drive bars and their related mechanisms return to their original position leaving the clips on the vessel and freeing the insturment from the vessel.

An advantage of the present invention is that the clips used may more aggressively grasp the vessel to be closed than prior art clips. The surface of the clips that contact the vessel to be closed may be scored or even include dimples and the like to ensure closure and prevent movement of the clip once it is placed on the vessel. Because less force is required to place the clip on the vessel there is reduced possibility of cutting or lacerating the vessel and greater assurance of positive closing of the vessel throughout the surgical procedure.

If desired, a detent or raised portion may be disposed on the inside of the slots in which the clips ride or move. Such a detent is placed in line with the connecting member of the clip so that when the housing is moved rearwardly to release the clips, the detent will crimp the connecting member of the clip to further insure positive placement of the clip.

While the spring steel flaps of the tweezer member of the instrument have been described and shown as uninterrupted surfaces, these diverging surfaces could comprise a plurality of fingers. By splitting or interrupting the surface into a plurality of fingers more than two clips could be applied at the same time.

The instrument may be made from various materials such as metals, preferably stainless steel, plastic preferably a polycarbonate resin and the like. Usually if the instrument is made from stainless steel the instrument will be reusable while if the instrument is made from plastic materials the instrument will be disposable. In certain embodiments of the instrument of the present invention the instrument may be designed to accept a replaceable cartridge of clips and this may be accomplished with either a reusable instrument or semi-disposable instrument which is meant to be used a number of times on a single patient.

Also, while the instrument has been described for placing ligating clips it should be appreciated that the feed member for the clips could be disengaged and the instrument used for grasping and manipulating vessels or tissue without ligation. Furthermore, if desired, means could be included with the instrument to heat the spring steel flaps so that the instrument could also be used for caurterizing vessels or tissue.

Surprisingly, the clips of the present invention will accept various sizes of vessels as the clip sizes itself as it is placed on the vessel.

A preferred clip of the present invention is shaped as described in conjunction with FIGS. 1 and 2. In this design the member connecting the legs of the clip not in line with the surface of the legs which will contact the vessel to be closed. This design allows the entire leg to be opened more or less uniformly along the entire length of the leg making the leg easier to part and placing less stress on the connecting member.

Another advantage of the present invention is that the clip and instrument of the present invention may be used in smaller diameter cannula than prior art clips used to close the same size vessels. Since the clip of the present invention is already in its closed configuration and no gripers or jaws are necessary to contact the outer surface of the clip in order to close the clip the overall diameter of the instrument may be reduced when compared to prior art instruments used for the same function. This allows the instrument to be used in smaller size cannula and reduces the trauma to the patent.

The clips of the present invention may be made from various well-known materials, for example, titanium, tantalum, stainless steel, the memory metals having super elastic characteristics and the like or the various plastic materials that have some resiliency such as the polyolefins, the glycolide-lactide polymers and similar plastic materials.

Having now described the present invention, it will be readily apparent to those skilled in the art that various modifications and alterations may be made to the present invention without departing from the spirit and scope thereof.

What is claimed is:

1. A method of applying a surgical fastener to body tissue comprising: providing a plurality of surgical fasteners, each said surgical fastener having facing tissue clamping portions that are movable between a normally closed tissue clamping position and an open tissue receiving position; locating each said surgical fastener within a fastener applying instrument with the tissue clamping portions thereof in the closed position, said applying instrument having an actuation mechanism that feeds a surgical fastener to the distal end of the instrument; positioning the distal end of said instrument adjacent the body tissue to be clamped; operating said actuation mechanism to feed each said surgical fastener toward the distal end of said instrument, and move the tissue clamping portions of said surgical fastener from the closed position to the open position so that said tissue clamping portions diverge from each other distally of said instrument; positioning the body tissue to be clamped between the tissue clamping portions of said surgical fastener; and returning the tissue clamping portions of said surgical fastener to the closed position to clamp the body tissue therebetween.

2. A method as set forth in claim 1 in which said surgical fastener is an occlusion fastener, and wherein said positioning step is performed by locating a tubular vessel between the tissue clamping portions of the occlusion fastener.

3. A method as set forth in claim 1 including the step of inserting the instrument through a cannula during an endoscopic procedure.

4. A method as set forth in claim 1 wherein said body tissue is compressed prior to returning the tissue clamping portions of the surgical fastener to the closed position.

5. A method as set forth in claim 4 including the step of cutting the body tissue after it is compressed and prior to returning the tissue clamping portions of the surgical fastener to the closed position.

6. A method as set forth in claim 1 in which a plurality of generally identical surgical fasteners are located in said instrument, and wherein said actuation mechanism is operated to successively feed surgical fasteners to the distal end of the instrument.

7. A method as set forth in claim 6 wherein said actuation mechanism is operated to successively feed surgical fasteners two at a time to the distal end of the instrument.

8. A method of applying a surgical fastener to body tissue, comprising the steps of: providing a surgical fastener having facing tissue clamping portions that are movable between a normally closed tissue clamping position and an open tissue receiving position; locating said surgical fastener within a fastener applying instrument with the tissue clamping portions thereof in the closed position; positioning the distal end of said instrument adjacent the body tissue to be clamped; compressing the tissue to be clamped at the distal end of said instrument between a pair of tissue compressing surfaces by effecting relative movement of at least one of said tissue compressing surfaces toward the other; feeding said surgical fastener toward the distal end of said instrument, and moving the tissue clamping portions of said surgical fastener from the closed position to the open position during said feeding step so that said tissue clamping portions diverge from each other distally of said instrument; positioning the compressed body tissue to be clamped between the tissue clamping portions of said surgical fastener; and returning the tissue clamping portions of said surgical fastener to the closed position to clamp the previously compressed body tissue therebetween.

9. A method as set forth in claim 8 in which the tissue compressing step is performed by simultaneously moving toward each other both tissue compressing surfaces of said pair of tissue compressing surfaces.

10. A method as set forth in claim 8 in which said surgical fastener is an occlusion fastener, and wherein said positioning step is performed by locating a tubular vessel between the tissue clamping portions of the occlusion fastener.

11. A method as set forth in claim 8 including the step of inserting the instrument through a cannula during an endoscopic procedure.

12. A method as set forth in claim 8 including the step of cutting the body tissue after it is compressed and prior to returning the tissue clamping portions of the surgical fastener to the closed position.

13. A method as set forth in claim 8 in which a plurality of generally identical surgical fasteners are located in said instrument, and wherein said actuation mechanism is operated to successively feed surgical fasteners to the distal end of the instrument.

14. A method as set forth in claim 13 wherein said actuation mechanism is operated to successively feed surgical fasteners two at a time to the distal end of the instrument.

15. A method of endoscopically successively applying surgical fasteners to body tissue, comprising the steps of: providing a plurality of surgical fasteners each having a pair of tissue clamping portions movable between an open position to receive body tissue therebetween, and a closed position to grip and retain body tissue therebetween, wherein said tissue clamping portions are biased toward said closed position; providing an instrument with a frame, and an elongated endoscopic portion extending from said frame within which said plurality of surgical fasteners are serially positioned, one behind the other, wherein the instrument includes an advancing mechanism including a manually operable handle mounted on said frame that successively distally advances said surgical fasteners one at a time to a distal end of said endoscopic portion; moving the tissue clamping portions of the surgical fastener at the distal end of said endoscopic portion to said open position, and positioning the tissue to be clamped between the tissue clamping portions of said surgical fastener; and releasing said tissue clamping portions after body tissue has been positioned therebetween, so that said tissue clamping portions move toward each other to grip and clamp the body tissue disposed therebetween.

16. A method as set forth in claim 15 in which said surgical fasteners are occlusion fasteners, and wherein the positioning step is performed by locating a tubular vessel between the tissue clamping portions of the occlusion fastener.

17. A method as set forth in claim 15 including the step of inserting the instrument through a cannula during an endoscopic procedure.

18. A method as set forth in claim 15 wherein said body tissue is compressed prior to returning the tissue clamping portions of the surgical fastener to the closed position.

19. A method as set forth in claim 18 including the step of cutting the body tissue after it is compressed and prior to returning the tissue clamping portions of the surgical fastener to the closed position.

20. A surgical instrument for applying a surgical fastener to body tissue, said surgical fastener having facing tissue clamping portions movable between a normally closed tissue clamping position and an open tissue receiving position, said instrument comprising: a housing having a proximal end and a distal end; a support within said housing that movably supports a plurality of said surgical fasteners with the tissue clamping portions thereof in said closed position; an opener at the distal end of the housing engageable with the tissue clamping portions of each said surgical fastener to move said tissue clamping portion to said open position; a manually operable actuating handle mounted at the proximal end of said housing; a driver within said housing operable by said actuating handle that moves each said surgical fastener axially within said housing toward the distal end thereof and (1) into engagement with said opener so that the tissue clamping portions are moved from the closed position to the open position to receive tissue therebetween, and (2) out of engagement with said opener so that the tissue clamping portions return from the open position to the normally closed tissue clamping position.

21. A surgical instrument as set forth in claim 20 in which said plurality of surgical fasteners are movably supported within said housing, and wherein said driver cooperates with said actuating handle to feed said at least one surgical fastener axially within said housing.

22. A surgical instrument as set forth in claim 21 wherein said driver cooperates with said actuating handle to simultaneously feed two of said surgical fasteners axially within said housing.

23. A surgical instrument for applying clips to body tissue, each clip including tissue gripping portions biased toward one another, said instrument comprising:

a clip holder for storing a plurality of said clips; a tissue compressing mechanism positioned at a distal end of said instrument; a feed mechanism for delivering a clip from said holder to said tissue compressing mechanism, with said gripping portions of the clip being disposed in spaced relationship with compressed tissue and diverging from each other distally of said instrument; and release means cooperating with the clip to permit the tissue gripping portions to move into gripping relationship with the compressed tissue.

24. A surgical instrument in accordance with claim 23, wherein each said clip comprises a pair of right angle members each having a pair of legs disposed at right angles to each other, and a connecting member joining said right angle members.

25. A surgical instrument in accordance with claim 23, wherein said tissue compressing mechanism comprises a pair of diverging surfaces.

26. A surgical instrument in accordance with claim 23, wherein said clip holder is configured to store a plurality of pairs of said clips, said feed mechanism being arranged to deliver each said pair of said clips from said holder to said tissue compressing mechanism.

* * * * *